US00PP20301P2

(12) United States Plant Patent
Chapman

(10) Patent No.: US PP20,301 P2
(45) Date of Patent: Sep. 15, 2009

(54) ***DIANTHUS* PLANT NAMED 'RED BEAUTY'**

(50) Latin Name: *Dianthus gratianopolitanus*
Varietal Denomination: Red Beauty

(76) Inventor: Douglas A. Chapman, 5618 Cabe Ford Rd., Durham, NC (US) 27705

( * ) Notice: Subject to any disclaimer, the term of this patent is extended or adjusted under 35 U.S.C. 154(b) by 3 days.

(21) Appl. No.: 12/218,309

(22) Filed: Jul. 14, 2008

(51) Int. Cl.
*A01H 5/00* (2006.01)

(52) U.S. Cl. ..... Plt./283

(58) Field of Classification Search ..... Plt./283
See application file for complete search history.

*Primary Examiner*—Kent L Bell
(74) *Attorney, Agent, or Firm*—Audrey Charles

(57) ABSTRACT

A new and distinct cultivar of *Dianthus* plant named 'Red Beauty', characterized by its deep red-colored flowers, silver gray-colored foliage, and compact, mounded, and low growing growth habit.

1 Drawing Sheet

Latin name of genus and species of plant claimed: *Dianthus gratianopolitanus.*
Variety denomination: 'Red Beauty'.

BACKGROUND OF THE INVENTION

The present invention relates to a new and distinct cultivar of *Dianthus* plant botanically known as *Dianthus gratianopolitanus* and hereinafter referred to by the cultivar name 'Red Beauty'.

The new cultivar originated in a controlled environment in Rougemont, N.C. during April 2007. The new *Dianthus* cultivar is a naturally occurring sport of *Dianthus gratianopolitanus* 'Firewitch', not patented, characterized by its bright magenta-colored flowers, silver gray-colored foliage, and compact, mounded growth habit. The new cultivar was discovered as a whole plant and selected during April 2007 in a controlled environment at Rougemont, N.C.

Asexual reproduction of the new cultivar by terminal stem cuttings since May 2007 at Rougemont, N.C. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Red Beauty' as a new and distinct cultivar of *Dianthus* plant:

1. Deep red-colored flowers;
2. Silver-gray-colored foliage; and
3. Compact, mounded and low growing growth habit.

Plants of the new cultivar differ from plants of the parent primarily in flower color and leaf width.

Of the many commercially available *Dianthus* cultivars, the most similar in comparison to the new cultivar is the parent 'Firewitch', not patented. However, in side by side comparisons, plants of the new cultivar differ from plants of 'Firewitch' in at least the following characteristics:

1. Plants of the new cultivar have a flower color different from plants of 'Firewitch'; and
2. Plants of the new cultivar have a larger flower diameter than plants of 'Firewitch'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Red Beauty'. The plants were grown in quart-size pots for approximately one year in a poly-covered coldframe at Rougemont, N.C.

DETAILED BOTANICAL DESCRIPTION

Figure 1:
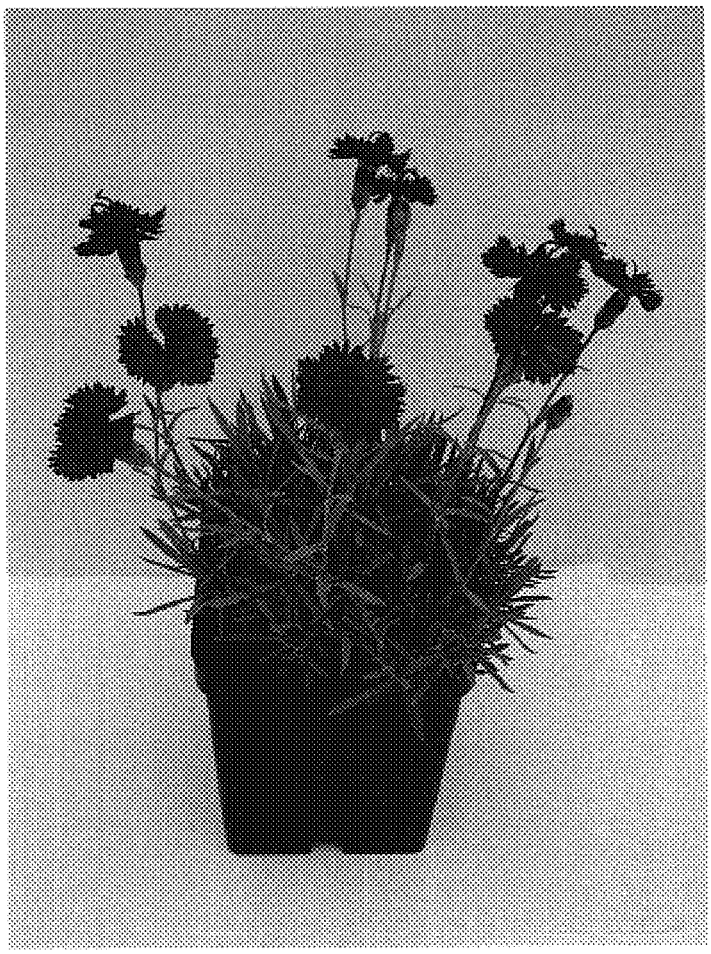
FIG. 1 illustrates a side view of the overall growth and flowering habit of 'Red Beauty'.
Figure 2:
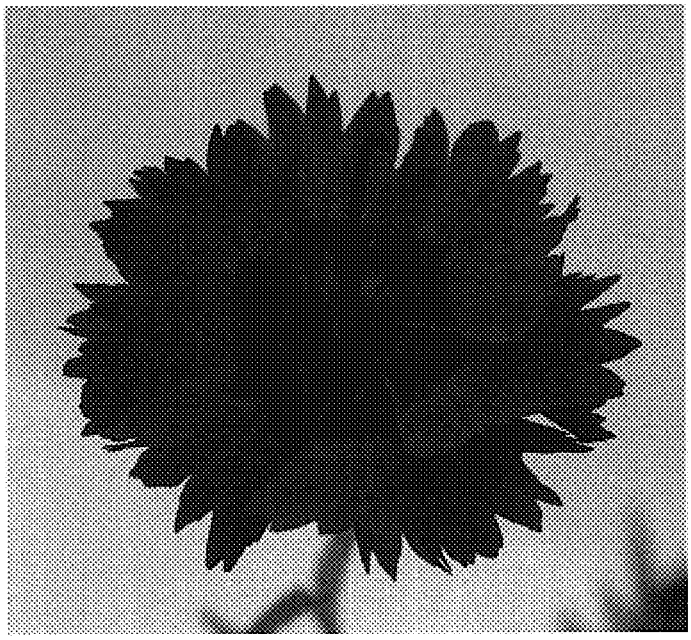
FIG. 2 illustrates a close-up view of an individual flower of 'Red Beauty'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 18, 2008 between 9:00 a.m. and 11:00 a.m. under natural light conditions in West Chicago, Ill.

The following descriptions and measurements describe plants produced from cuttings from stock plants and grown in a poly-covered coldframe under conditions comparable to those used in commercial practice. The plants were grown in Rougemont, N.C. in quart-size pots for approximately one year utilizing a soilless growth medium. During this time greenhouse temperatures ranged from highs of approximately 60° F. to 70° F. (15° C. to 21° C.) and lows of approximately 45° F. to 49° F. (7° C. to 9° C.). The plants were dormant during winter months with an average greenhouse temperature of 50° F. (10° C.) during the day and an average of 40° F. (5° C.) during the night. Greenhouse light levels of 7,500 footcandles to 8,500 footcandles were typical during sunny days. Measurements and numerical values represent averages of typical plants.

Botanical classification: *Dianthus gratianopolitanus* cultivar 'Red Beauty'.

Parentage:

*Parent.*—'Firewitch', not patented.

Propagation:

*Type cutting.*—Terminal stem.

*Time to initiate roots.*—Approximately 10 to 14 days.

*Time to produce a rooted cutting.*—Approximately 28 to 30 days.

*Root description.*—Fine, fibrous.

*Rooting habit.*—Freely branching.

Plant description:

*Commercial crop time.*—Approximately 12 to 14 weeks from a rooted cutting to finish in a quart-sized pot.

*Growth habit and general appearance.*—Compact, mounded and low-growing.

*Size.*—Height from soil level to top of plant plane: Approximately 18.0 cm. Width: Approximately 12.5 cm.

*Branching habit.*—Freely branching, pinching improves basal branching. Quantity of flowering stems per plant: Approximately 13.

*Flowering stem.*—Strength: Strong. Length: Approximately 14.5 cm. Diameter: Approximately 1.5 cm. Length of central internode: Approximately 2.5 cm. Texture: Glabrous. Color of young and mature stems: Glaucous, 147A with the waxy bloom imparting an overall tonality of more blue than 188A.

Foliage description:

*General description.*—Quantity of leaves per flowering stem: Approximately 12. Fragrance: None. Form: Simple. Arrangement: Opposite.

*Leaves.*—Aspect: Acute angle to stem. Shape: Linear. Margin: Entire with ciliation. Apex: Acute. Base: Sessile, decurrent. Venation pattern: Parallel, linear. Length of mature leaf: Approximately 3.7 cm. Width of mature leaf: Approximately 3.0 mm. Texture of upper and lower surfaces: Glabrous. Color of upper surface of young and mature foliage: Glaucous, 147A with the waxy bloom imparting an overall tonality of more blue than 188A. Venation is indistinguishable. Color of lower surface of young and mature foliage: Glaucous, lighter than 147A with the waxy bloom imparting an overall tonality of more blue than 188A. Venation is indistinguishable.

Flowering description:

*Flowering habit.*—'Red Beauty' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single, salverform, persistent. Quantity per plant: Approximately 10. Fragrance: Spicy, clove-like.

*Bud.*—Rate of opening: Generally takes 3 to 5 days for bud to progress from first color to fully open flower. Quantity per plant: 3.

*Bud just before opening.*—Shape: Cylindrical. Length: Approximately 1.7 cm. Diameter: Approximately 7.0 mm. Texture: Glabrous. Color: Glaucous, 146A with an overlay of 187A at apex.

*Corolla.*—Diameter: Approximately 3.2 cm. Depth: Approximately 3.0 cm.

*Petals/petaloids.*—Quantity: 5 to 7. Shape: Fan-shaped, tapering toward base. Appearance: Velvety. Margin: Entire with an erose outer edge. Apex: Rounded. Base: Attenuate. Length from throat: Approximately 1.4 cm. Width: Approximately 1.9 cm. Texture of upper surface: Sparsely pubescent. Texture of lower surface: Glabrous. Color of upper surface when first and fully open: Between 61B and 61A with a ring of darker than 71A surrounding throat opening. Color of lower surface when first and fully open: Closest to 59C.

*Corolla tube.*—Length: Approximately 1.7 cm. Diameter at proximal end: Approximately 3.0 mm. Diameter at distal end: Approximately 4.0 mm. Texture of inner and outer surfaces: Glabrous. Color of inner surface: Base of 145D transitioning toward throat opening through a small band of 155D to 70B. Color of outer surface: Base of 145D transitioning toward throat opening to 70B.

*Calyx.*—Shape: Sepals fused forming a cylindrical shape with 6 acute tips. Length: Approximately 1.6 cm. Diameter: Approximately 6.0 mm. Texture of upper and lower surfaces: Glabrous. Color of upper surface: 144A. Color of lower surface: Glaucous, 146A with an overlay of 187A at apices and base.

*Epicalyx.*—Quantity: 4 bracts arranged in two pairs. Shape: Deltoid. Margin: Entire. Apex: Acute. Base: Truncate. Length: Approximately 7.0 mm. Width: Approximately 6.0 mm. Texture of upper and lower surfaces: Glabrous. Color of upper and lower surfaces: Glaucous, 137A with lateral margins of N187A.

*Peduncle.*—Strength: Strong. Aspect: Erect. Length: Approximately 2.9 cm. Diameter: 1.0 mm. Texture: Glabrous. Color: Glaucous, lighter than 147A with the waxy bloom imparting an overall tonality of more blue than 188A.

*Reproductive organs.*—Androecium: Stamen quantity: Approximately 15, connate lower third. Filament length: Approximately 6.0 mm. Filament color: 155D. Anther shape: Oblong to malformed. Anther length: Approximately 1.0 mm. Anther color: 161C. Pollen amount: None observed. Gynoecium: Pistil quantity: 1 per flower, 2-parted style. Pistil length: Approximately 3.4 cm. Stigma shape: Linear, tapering down the length of the style, recurved. Stigma/style length: Approximately 2.4 cm. Stigma color: N79A. Style color: Pure white at base transitioning at midpoint to white with an overlay N79B that intensifies toward tip. Ovary length: Approximately 1.0 cm. Ovary diameter: Approximately 5.0 mm. Ovary color: 144A.

Seed and fruit production: Neither seed nor fruit production has been observed.

Disease and pest resistance: Resistance to pathogens and pests common to *Dianthus* has not been observed.

What is claimed is:

1. A new and distinct cultivar of *Dianthus* plant named 'Red Beauty', substantially as herein shown and described.

* * * * *